US00PP15127P2

(12) United States Plant Patent
Arimitsu

(10) Patent No.: US PP15,127 P2
(45) Date of Patent: Aug. 31, 2004

(54) VERBENA PLANT NAMED 'BODCOMCAR'

(50) Latin Name: *Verbena hybrida*
Varietal Denomination: Bodcomcar

(75) Inventor: Yoshiro Arimitsu, Lompoc, CA (US)

(73) Assignee: John Bodger + Sons Co., South El Monte, CA (US)

( * ) Notice: Subject to any disclaimer, the term of this patent is extended or adjusted under 35 U.S.C. 154(b) by 0 days.

(21) Appl. No.: 10/684,565

(22) Filed: Oct. 13, 2003

(51) Int. Cl.[7] ..... A01H 5/00
(52) U.S. Cl. ..... Plt./308
(58) Field of Search ..... Plt./308

*Primary Examiner*—Anne Marie Grunberg
(74) *Attorney, Agent, or Firm*—C. A. Whealy

(57) ABSTRACT

A new and distinct cultivar of Verbena plant named 'Bodcomcar', characterized by its compact, upright and mounded plant habit; freely branching habit; dense and bushy growth habit; dark green-colored leaves; and red purple-colored flowers with flowers held above and beyond the foliage.

1 Drawing Sheet

Botanical classification/cultivar designation: Verbena hybrida cultivar Bodcomcar.

BACKGROUND OF THE INVENTION

The present Invention relates to a new and distinct cultivar of Verbena plant, botanically known as Verbena hybrida, and hereinafter referred to by the name 'Bodcomcar'.

The new Verbena is a product of a planned breeding program conducted by the Inventor in Lompoc, Calif. The objective of the breeding program is to develop new Verbena cultivars with a dense and bushy growth habit, numerous flowers, and interesting flower and foliage colors.

The new Verbena originated from a self-pollination made by the Inventor in July, 1989 of a proprietary Verbena hybrida selection identified as 6L1535, not patented. The cultivar Bodcomcar was discovered and selected by the Inventor as a flowering plant within the progeny from this self-pollination in a controlled environment in Lompoc, Calif.

Asexual reproduction of the new cultivar by terminal cuttings in a controlled environment in Lompoc, Calif. has shown that the unique features of this new Verbena are stable and reproduced true to type in successive generations of asexual reproduction.

SUMMARY OF THE INVENTION

The following traits have been repeatedly observed and are determined to be the unique characteristics of 'Bodcomcar'. These characteristics in combination distinguish 'Bodcomcar' as a new and distinct cultivar:

1. Compact, upright and mounded plant habit.
2. Freely branching habit; dense and bushy growth habit.
3. Dark green-colored leaves.
4. Red purple-colored flowers with flowers held above and beyond the foliage.

Plants of the new Verbena differ primarily from plants of the parent selection in plant habit and flower coloration.

Plants of the new Verbena differ primarily from plants of the cultivar Bodcomros, disclosed in a U.S. Plant patent application Ser. No. 10/684,576, in flower coloration.

Plants of the new Verbena can be compared to plants of the cultivar Obsession Carmine Eye, not patented. In side-by-side comparisons conducted in Lompoc, Calif., plants of the new Verbena differed primarily from plants of the cultivar Obsession Carmine Eye in plant and flower form as plants of the cultivar Obsession Carmine Eye are more mounded and have narrower petals than plants of the new Verbena.

Plants of the new Verbena can also be compared to plants of the cultivar Sandy Rose, not patented. In side-by-side comparisons conducted in Lompoc, Calif., plants of the new Verbena differed primarily from plants of the cultivar Sandy Rose in plant form as plants of the cultivar Sandy Rose are more upright and taller than plants of the new Verbena.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photograph differ slightly from the color values cited in the detailed botanical description which accurately describe the colors of the new Verbena.

The photograph at the top of the sheet comprises a side perspective view of a typical flowering plant of 'Bodcomcar' grown in a container.

The photograph at the bottom of the sheet comprises a close-up view of typical inflorescences, flowers and leaves of 'Bodcomcar'.

DETAILED BOTANICAL DESCRIPTION

The cultivar Bodcomcar has not been observed under all possible environmental conditions. The phenotype may vary somewhat with variations in environment such as temperature and light intensity without, however, any variance in genotype. The aforementioned photographs and following observations and measurements describe plants grown in Lompoc, Calif., under commercial practice during the summer in a polycarbonate-covered greenhouse with day temperatures about 21 to 27° C., night temperatures about 16 to 18° C., and light levels about 4,000 to 8,000 foot-candles. Cuttings were planted in 10-cm containers, pinched one time, and grown for about seven weeks. In the following description, color references are made to The Royal Horticultural Society Color Chart, 1995 Edition, except where general terms of ordinary dictionary significance are used.

Botanical classification: Verbena hybrida cultivar Bodcomcar.

Parentage: Self-pollination of a proprietary Verbena hybrida selection identified as 6L1535, not patented.

*Lateral branches.*—Length: About 13 cm. Diameter: About 2 mm. Internode length: About 1.75 cm. Texture: Pubescent. Color: 146D.

*Foliage description.*—Arrangement: Opposite, simple. Length: About 3.6 cm. Width: About 2 cm. Shape: Deltoid. Apex: Broadly acute. Base: Acute. Margin: Irregularly crenate. Texture, upper and lower surfaces: Coarse, pubescent. Venation pattern: Pinnate.

Propagation:

*Type cutting.*—Terminal cuttings.

*Time to initiate roots, summer.*—About 7 to 10 days at 26° C.

*Time to initiate roots, winter.*—About 21 days at 26° C.

*Time to produce a rooted cutting or liner, summer.*—About 21 days at 26° C.

*Time to produce a rooted cutting or liner, winter.*—About 28 days at 26° C.

*Root description.*—Fine, fibrous; white in color.

*Rooting habit.*—Freely branching; dense.

Plant description:

*Form.*—Compact, upright and mounded plant habit.

*Growth and branching habit.*—Moderately vigorous and freely-branching with about 10 lateral branches developing after the pinch, dense and bushy growth habit.

*Plant height.*—About 15 cm.

*Plant diameter or spread.*—About 22 cm. Color: Developing foliage, upper surface: 137A. Developing foliage, lower surface: 147B. Fully expanded, upper surface: 147A. Fully expanded, lower surface: 147B. Venation, upper surface: 143C. Venation, lower surface: 143D. Petiole: Length: About 1 cm. Diameter: About 2 mm. Color: 143C.

Flower description:

*Flower type and habit.*—Single upright salverform flowers arranged on compact terminal racemes; flowers sessile. Freely flowering with about 15 flowers and flower buds per raceme; about two to three racemes per lateral branch. Inflorescences positioned above and beyond the foliage. Flowers last about four days under greenhouse conditions. Flowers not persistent.

*Fragrance.*—None detected.

*Flowering season.*—In the garden, flowering is continuous from spring until fall.

*Inflorescence height.*—About 4.5 cm.

*Inflorescence diameter.*—About 6.5 cm.

*Flower size.*—Diameter: About 2.5 cm. Tube length: About 2.2 cm. Throat diameter: About 3 mm. Tube diameter, at base: About 2 mm.

*Flower buds.*—Rate of opening, from showing color to fully open flower: About two days. Length: About 1.3 cm. Diameter, apex: About 4 mm. Diameter, base: About 2.5 mm. Shape: Tubular, oblong. Color: 65B.

*Petals.*—Quantity/arrangement: Five per flower fused at base. Lobe length: About 1.4 cm. Lobe width: About 1.2 cm. Shape: Roughly cordate. Apex: Emarginate. Margin: Entire. Texture, upper and lower surfaces: Velvety, smooth. Color: When opening, upper surface: Brighter than 53A. When opening, lower surface: 54A. Fully opened, upper surface: 57A. Fully opened, lower surface: 57D. Throat: 145C. Tube: 157A to 145C.

*Sepals.*—Quantity/arrangement: Five, fused into a tube. Length: About 1.3 cm. Diameter: About 3 mm. Shape: Ligulate. Apex: Acute. Margin: Entire. Texture, upper and lower surfaces: Coarse, pubescent. Color, upper surface: 143D. Color, lower surface: 143B.

*Peduncles.*—Length: About 5 cm. Diameter: About 1.5 mm. Angle: Upright to about 45° from vertical. Strength: Strong. Color: 143A.

*Reproductive organs.*—Stamens: Quantity per flower: Four; adnate to pistil. Anther shape: Oval. Anther length: Less than 1 mm. Anther color: 145B. Pollen amount: Scarce. Pollen color: 145B. Pistils: Quantity per flower: One. Pistil length: About 1.8 cm. Stigma shape: Bi-parted. Stigma color: 144B. Style length: About 1.6 cm. Style color: 144D. Ovary color: 144C to 144D.

*Fruit/seed.*—Fruit and seed production has not been observed.

Disease/pest resistance: Plants of the new Verbena have not been observed to be resistant to pathogens and pests common to Verbena.

Temperature tolerance: Plants of the new Verbena have been observed to be tolerant to temperatures ranging from 2 to 40° C.

It is claimed:

1. A new and distinct cultivar of Verbena plant named 'Bodcomcar', as illustrated and described.

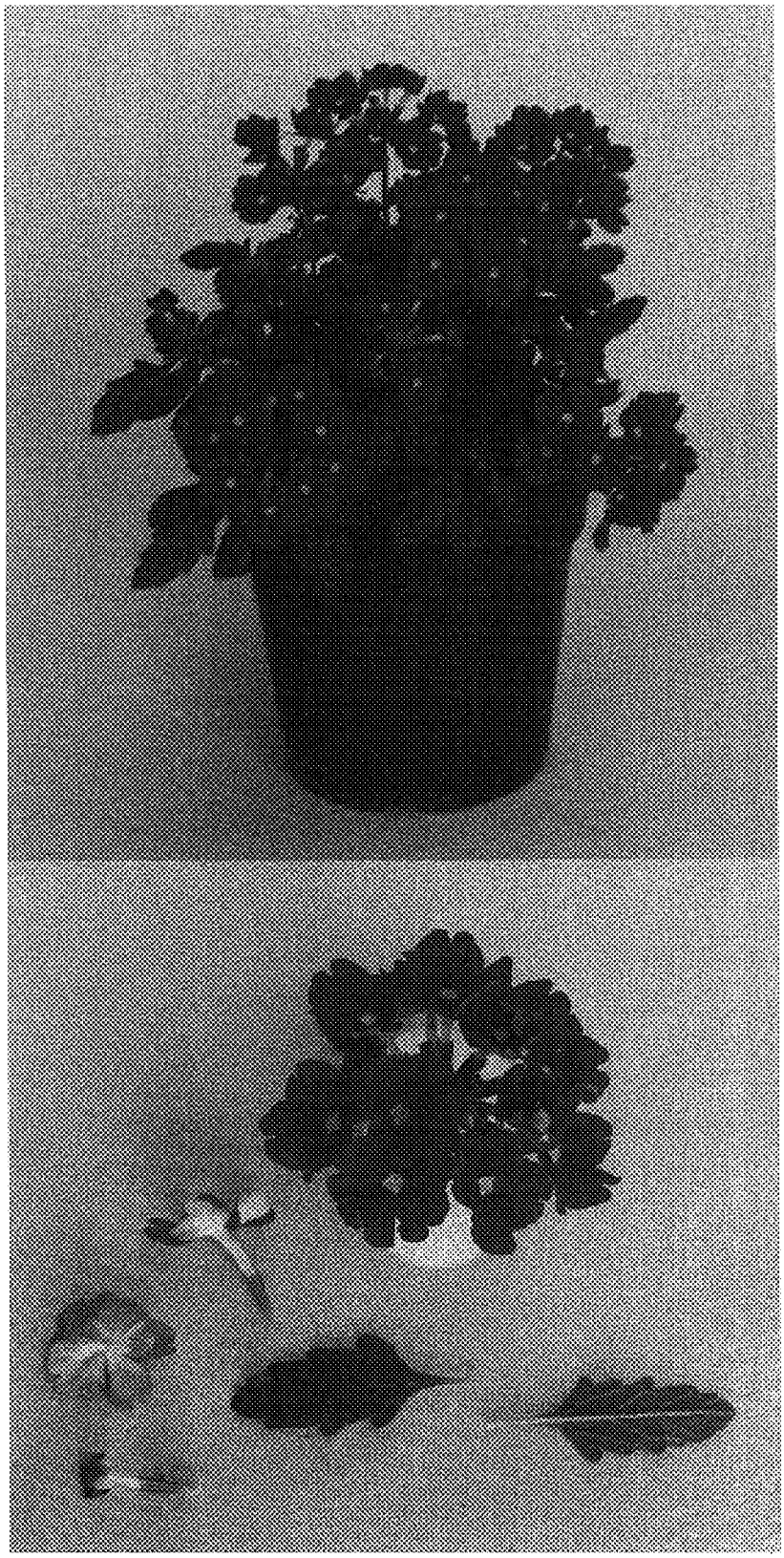

* * * * *